United States Patent [19]

Meier et al.

[11] Patent Number: Plant 6,280

[45] Date of Patent: Sep. 6, 1988

[54] KENTUCKY BLUEGRASS

[75] Inventors: Virgil D. Meier, Marysville, Ohio; Richard Schneider, Port Republic, Md.; Eugene Mayer, Marysville, Ohio

[73] Assignee: The O.M. Scott & Sons Company, Marysville, Ohio

[21] Appl. No.: 910,146

[22] Filed: Sep. 19, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—James B. Raden

[57] ABSTRACT

A variety of Kentucky bluegrass having a high level of disease resistance, excellent turf performance in the sun and shade, and a good to medium level of seed yield potential.

1 Drawing Sheet

BACKGROUND

Kentucky bluegrasses have been disclosed in U.S. Plant Pat. No. 3,156 which issued on May 9, 1972; U.S. Plant Pat. No. 3,186 which issued on May 23, 1972; U.S. Plant Pat. No. 4,336 which issued on Nov. 28, 1978; and U.S. Plant patent application, Ser. No. 872,537, filed June 10, 1986.

SUMMARY OF THE VARIETY

The present invention relates to a new and distinct variety of *Poa pratensis* which has been designated Ba 72-500 Kentucky bluegrass.

Ba 72-500 plant material originated by crossing a Kentucky bluegrass plant disclosed in U.S. plant application Ser. No. 872,537, the seed parent, with a pollen parent plant. As a result of this breeding, a distinct variety was produced and asexually propagated by rhizones, tillers and disseminules.

Ba 72-500 Kentucky bluegrass reproduced asexually by propagules, i.e., by tillers and rhizomes and by disseminules (modified caryopses produced by apomixis). Progeny plants have been produced which are indistinguishable from the mother plant.

Ba 72-500 has a number of highly desirable characteristics including a good level of resistance to Helminthosporium spp. that causes leaf spot, melting out, and crown rot; *Ustilago striiformis* that causes stripe smut; *Erysiphe graminis* that causes powdery mildew; and Puccinia spp. that causes rust; a leafy turf type growth habit; moderately wide leaf blades; an attractive green color which can be maintained throughout the entire growing season; good turf performance as evidenced by consistently high performance scores in tests throughout the U.S.A. and Canada, and a good-to-medium seed yield potential in the bluegrass seed production region of the U.S.A.

In comparison with its seed parent, the new variety is more shade tolerant and has better resistance to powdery mildew and rust.

BRIEF DESCRIPTION OF THE DRAWING

FIG. 1 is a photograph of Ba- 72-500 Kentucky bluegrass plant in the vegetative stage including the extensive root and rhizome system;

FIG. 2 is a photograph of Ba 72-500 Kentucky bluegrass panicle; and

FIG. 3 is a photograph of Ba 72-500 Kentucky bluegrass seed.

DETAILED DESCRIPTION OF THE VARIETY

Ba 72-500 Kentucky bluegrass (*Poa pratensis* L.) is perennial with creeping rhizomes forming a moderately dense turf. When plants winter in the field with freezing temperatures and then are brought into the greenhouse during late winter to continue growth undisturbed by clipping under moderate temperatures (60°-80° F.), culms are erect averaging 439 mm tall with an average of 2.7 nodes per culm. The uppermost internode averages 9.8 cm, and the peduncle averages 12.9 cm in length and 0.660 mm in thickness. The flag leaf averages 4.1 cm in length, 3.2 mm in width, and 0.112 mm in thickness. The panicle is nodding with an average length of 6.8 cm, width of 3.8 cm, and 5.0 whorls. The lowest whorl has an average of 4.0 branches and the third whorl from the bottom of the panicle has an average of 2.4 branches. The average spikelet at the tip of a branch in the lowest whorl is 5.1 mm in length and has 4.2 florets with an outer glume of 3.1 mm in length and an inner glume of 3.4 mm in length. A similar spikelet from the third whorl from the bottom is 5.0 mm in length and has 3.9 florets with an outer glume of 3.1 mm in length and an inner glume of 3.4 mm in length. After the seed has been conditioned, the lemma has a rough keel with occasional long, fine hairs at the base. The seed of Ba 72-500 is 2.77 mm in length and 0.80 mm in width with approximately 1,300,105 seeds per pound. Comparisons of Ba 72-500 and other bluegrasses for seed measurements and seed counts per pound are found in Tables 1 and 2.

TABLE 1

Seed Measurements of Ba 72-500 and Other Bluegrass Varieties After Conditioning.

| Variety | Length (mm) | Width (mm) |
|---|---|---|
| Ba 72-500 | 2.77 | O.80 |
| Baron | 3.07 | 0.86 |
| Bristol | 2.73 | 0.80 |
| Nassau | 2.96 | 0.78 |
| Newport | 2.76 | 0.71 |
| Park | 3.04 | 0.72 |
| Ram I | 3.51 | 0.84 |
| Victa | 3.20 | 0.86 |
| LSD (.05) | 0.19 | 0.06 |

TABLE 2

Seed Counts Per Pound of Ba 72-500 and Other Bluegrass Varieties After Conditioning

| | Number of Seeds Per Pound |
|---|---|
| Ba 72-500 | 1,300,105 |
| Adelphi | 1,383,976 |
| America | 1,659,824 |
| Gnome | 1,017,641 |
| Baron | 1,051,693 |
| Birka | 1,223,530 |
| Bonnieblue | 1,135,303 |
| Bristol | 1,270,821 |
| Classic | 1,250,316 |
| Eclipse | 1,335,668 |
| Georgetown | 1,232,913 |
| Glade | 1,108,441 |
| Kenblue | 1,463,923 |
| Merit | 1,109,728 |
| Nassau | 1,127,130 |
| Newport | 1,226,481 |
| Park | 1,248,349 |
| Sydsport | 1,355,644 |
| Vantage | 1,555,303 |
| Victa | 1,038,298 |

Since environmental conditions such as soil and climate influence morphological characteristics to some extent, comparisons of morphological characteristics of Ba 72-500 are made with other Kentucky bluegrass varieties in Tables 3–7.

TABLE 3

Morphological Comparisons of Ba 72-5OO and Other Bluegrass Varieties Grown as Unmowed Spaced Plants in the Field at Marysville, Ohio.

| | Mature Plant Height (cm) 2 Year Mean | Leaf Blade Width 2 Year Mean | Panicle Density 2 Year Mean | Seedhead Weight 2 Year Mean |
|---|---|---|---|---|
| Ba 72-500 | 46 | 2.4 | 6 | 335 |
| Nugget | 36 | 2.0 | 5 | 225 |
| Glade | 53 | 2.2 | 7 | 314 |
| Vantage | 67 | 2.5 | 6 | 786 |
| Adelphi | 53 | 2.3 | 6 | 396 |
| Park | 55 | 2.2 | 6 | 361 |
| Bristol | 55 | 2.3 | 7 | 385 |
| Parade | 53 | 2.5 | 5 | 372 |
| A-34 | 65 | 2.1 | 8 | 384 |
| Kenblue | 63 | 2.4 | 6 | 498 |
| Victa | 46 | 3.0 | 7 | 442 |
| Merion | 49 | 2.2 | 7 | 191 |
| LSD (.05) | 18 | 0.7 | 2 | 427 |

Ratings:
Leaf Blade Width: 1–4,4 = wide blades
Panicle Density: 0–9,9 = very high panicle density
Seedhead Weight: Weight (mg) of three panicles

TABLE 4

Morphological Comparison of Panicles of Ba 72-500 and Other Bluegrass Varieties in the Greenhouse at Marysville, Ohio.

| Variety | Panicle Nodding* | Panicle Length (cm) | Panicle Width (cm) | Number of Whorls Per Panicle |
|---|---|---|---|---|
| Ba 72-500 | 2.0 | 6.8 | 3.8 | 5.0 |
| Baron | 1.0 | 7.8 | 4.1 | 5.2 |
| Bristol | 2.0 | 9.7 | 5.0 | 5.0 |
| Nassau | 2.0 | 10.0 | 6.0 | 5.0 |
| Newport | 2.0 | 10.3 | 4.4 | 4.5 |
| Park | 1.6 | 9.0 | 3.7 | 4.0 |
| Ram I | 2.0 | 9.0 | 4.7 | 4.0 |
| Victa | 1.2 | 7.5 | 4.1 | 5.4 |
| LSD (.05) | 0.5 | 1.6 | 1.0 | 0.8 |

| Variety | Number of Branches: Lower Whorl | Number of Branches: Third Whorl | Peduncle Length (cm) | Peduncle Width (mm) |
|---|---|---|---|---|
| Ba 72-500 | 4.0 | 2.4 | 12.9 | 0.660 |
| Baron | 3.8 | 2.5 | 12.7 | 0.559 |
| Bristol | 3.3 | 2.7 | 15.0 | 0.686 |
| Nassau | 3.0 | 2.0 | 8.0 | 0.533 |
| Newport | 2.3 | 2.3 | 18.0 | 0.558 |
| Park | 4.3 | 3.7 | 14.3 | 0.787 |
| Ram I | 2.5 | 2.0 | 18.5 | 0.610 |
| Victa | 4.4 | 3.4 | 12.2 | 0.711 |
| LSD (.05) | 0.7 | 0.8 | 3.7 | 0.018 |

*Panicle nodding rated 1 = erect, 2 = nodding.

TABLE 5

Morphological Comparison of Culms and Flag Leaves of Ba 72-500 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Ba 72-500 | 4.1 | 3.2 | 0.112 |
| Baron | 4.5 | 3.2 | 0.119 |
| Bristol | 5.5 | 3.4 | 0.127 |
| Nassau | 6.2 | 3.1 | 0.127 |
| Newport | 6.1 | 3.5 | 0.135 |
| Park | 4.2 | 2.6 | 0.109 |
| Ram I | 4.7 | 3.1 | 0.127 |
| Victa | 5.9 | 4.0 | 0.124 |
| LSD (.05) | 1.8 | 0.6 | 0.013 |

| Variety | Top Internode Length (cm) | Culm Length (mm) | Number of Nodes Per Culm |
|---|---|---|---|
| Ba 72-500 | 9.8 | 439 | 2.7 |
| Baron | 10.1 | 482 | 2.5 |
| Bristol | 11.3 | 522 | 2.7 |
| Nassau | 11.2 | 450 | 2.5 |
| Newport | 11.2 | 547 | 2.3 |
| Park | 13.0 | 578 | 3.0 |
| Ram I | 10.2 | 527 | 3.0 |
| Victa | 10.6 | 474 | 2.4 |
| LSD (.05) | 2.1 | 79 | 0.6 |

TABLE 6

Morphological Comparison of Spikelets and Florets of Ba 72-500 and Other Bluegrass Varieties in the Greenhouse at Marysville, Ohio.

| Variety | Spikelet Length (mm): Lowest Whorl | Spikelet Length (mm): Third Whorl | Number of Florets per Spikelet: Lowest Whorl | Number of Florets per Spikelet: Third Whorl |
|---|---|---|---|---|
| Ba 72-500 | 5.1 | 5.0 | 4.2 | 3.9 |
| Baron | 5.0 | 5.0 | 3.7 | 3.8 |
| Bristol | 6.2 | 6.0 | 5.7 | 5.3 |
| Nassau | 4.6 | 4.6 | 4.5 | 4.5 |
| Newport | 5.3 | 5.2 | 5.2 | 5.2 |
| Park | 6.5 | 6.7 | 5.2 | 4.7 |
| Ram I | 4.7 | 5.2 | 5.2 | 5.5 |
| Victa | 5.2 | 5.0 | 3.8 | 3.8 |
| LSD (.05) | 0.9 | 0.8 | 1.1 | 1.0 |

| Variety | Glume Length (mm) Outer: Lowest Whorl | Glume Length (mm) Outer: Third Whorl | Glume Length (mm) Inner: Lowest Whorl | Glume Length (mm) Inner: Third Whorl |
|---|---|---|---|---|
| Ba 72-500 | 3.1 | 3.1 | 3.4 | 3.4 |
| Baron | 2.9 | 2.8 | 3.4 | 3.3 |
| Bristol | 3.4 | 3.3 | 3.7 | 3.9 |
| Nassau | 2.3 | 2.4 | 2.7 | 2.7 |
| Newport | 2.6 | 2.5 | 2.9 | 2.9 |
| Park | 3.0 | 3.2 | 3.5 | 3.7 |
| Ram I | 2.6 | 2.4 | 2.9 | 2.7 |
| Victa | 2.8 | 3.0 | 3.3 | 3.3 |

TABLE 6-continued

Morphological Comparison of Spikelets and Florets of Ba 72-500 and Other Bluegrass Varieties in the Greenhouse at Marysville, Ohio.

| | | | | |
|---|---|---|---|---|
| LSD (.05) | 0.5 | 0.4 | 0.4 | 0.4 |

TABLE 7

Morphological Comparison of Leaves of Ba 72-500 and Other Bluegrass Varieties in the Greenhouse at Marysville, Ohio.

| Variety | Ligule Length (mm) | Leaf Length (mm) | Leaf Width (mm) | Leaf Angle (Degrees From Horizontal) |
|---|---|---|---|---|
| Ba 72-500 | 0.25 | 204 | 4.1 | 50 |
| Baron | 0.30 | 313 | 4.4 | 63 |
| Bristol | 0.30 | 253 | 4.3 | 37 |
| Nassau | 0.22 | 226 | 3.5 | 39 |
| Newport | 0.22 | 251 | 4.1 | 50 |
| Park | 0.33 | 329 | 4.2 | 44 |
| Ram I | 0.18 | 188 | 3.7 | 40 |
| Victa | 0.28 | 235 | 4.3 | 52 |
| LSD (.05) | 0.11 | 49 | 0.6 | 10 |

| Variety | Hairs[a] Around Ligule on Upper Surface of the Leaf | Hairs[a] on Collar | Hairs[b] on Ligule |
|---|---|---|---|
| Ba 72-500 | 1.0 | 3.5 | 2.7 |
| Baron | 1.0 | 5.0 | 4.0 |
| Bristol | 1.3 | 4.7 | 4.3 |
| Nassau | 2.7 | 5.0 | 1.0 |
| Newport | 1.0 | 4.0 | 0.8 |
| Park | 1.0 | 1.7 | 0.0 |
| Ram I | 1.0 | 3.7 | 0.3 |
| Victa | 1.0 | 3.3 | 2.2 |
| LSD (.05) | 0.3 | 1.4 | 1.8 |

[a]Hairs around ligule and on collar rated 1-5: 1 = none, 5 = many.
[b]Hairs on ligule rated 0-5: 0 = none, 5 = many.

Ba 72-500 has performed very well throughout the U.S.A. and Canada as exhibited by high turf quality ratings in ten different locations as the comparisons show in Table 8.

TABLE 8

Comparison of the Turf Quality of Ba 72-500 and Other Bluegrass Varieties in the U.S.A. and Canada

| Variety | St. Louis Missouri 1 Year Mean | Guelph Ontario 2 Year Mean | Winnipeg Manitoba 2 Year Mean | Beltsville Maryland 1 Year Mean |
|---|---|---|---|---|
| Ba 72-500 | 3.2 | 7.7 | 6.9 | 5.8 |
| A-34 | | | 6.6 | 5.6 |
| Adelphi | 2.9 | | | 5.9 |
| Admiral | | | 6.0 | |
| America | 2.8 | | | |
| Aquila | | | 7.1 | |
| Banff | | | | 4.8 |
| Baron | 2.7 | | 6.2 | 5.3 |
| Birka | 2.3 | | | |
| Bonnieblue | | | | 5.0 |
| Bono | | | | |
| Bristol | 2.7 | | | 5.0 |
| Columbia | | | | 4.9 |
| Eclipse | | | | 5.9 |
| Enmundi | | | | 5.5 |
| Fylking | | | | 4.9 |
| Geary | | | | |
| Geronimo | | | | |
| Glade | 2.8 | | | 5.3 |
| Gnome | 2.9 | 7.0 | | |
| Kenolue | | | | |
| Merion | | 6.7 | | 5.3 |
| Merit | 2.8 | | 6.5 | 6.1 |
| Midnight | | | | 5.5 |
| Monopoly | | | | 4.9 |
| Mystic | | | 6.6 | |

TABLE 8-continued

Comparison of the Turf Quality of Ba 72-500 and Other Bluegrass Varieties in the U.S.A. and Canada

| | | | | |
|---|---|---|---|---|
| Nassau | | | 5.9 | 4.5 |
| Newport | | | | |
| Nugget | | | 7.1 | |
| Parade | | | | 5.0 |
| Park | 1.8 | 6.7 | | |
| Ram I | | | | 4.6 |
| SO Common | | | | |
| Shasta | | 6.7 | 7.1 | |
| Sydsport | 2.7 | | | 5.8 |
| Touchdown | 2.7 | | 6.8 | 5.8 |
| Trampas | | | 6.3 | |
| Vantage | 2.6 | | | 5.5 |
| Victa | 2.8 | | | 5.5 |
| Wabash | | | | |

| Variety | Adelphia New Jersey 2 Year Mean | Lincoln Nebraska 2 Year Mean | Agassiz British Columbia 1 Year Mean |
|---|---|---|---|
| Ba 72-500 | 6.1 | 6.0 | 5.4 |
| A-34 | | 6.2 | |
| Adelphi | 6.4 | 6.1 | |
| Admiral | | | |
| America | | | |
| Aquila | 5.7 | | |
| Banff | | | |
| Baron | 6.4 | 5.6 | |
| Birka | 5.9 | 5.9 | |
| Bonnieblue | 6.7 | 5.8 | |
| Bono | | | 5.2 |
| Bristol | 6.5 | 5.9 | 6.1 |
| Columbia | 5.9 | | |
| Eclipse | 7.2 | 5.8 | |
| Enmundi | 6.3 | 5.9 | |
| Fylking | 5.7 | 6.1 | |
| Geary | 3.6 | | |
| Geronimo | | | 5.1 |
| Glade | 6.7 | 6.4 | |
| Gnome | 6.4 | | |
| Kenolue | 3.3 | | |
| Merion | 6.0 | 5.9 | 5.3 |
| Merit | 6.2 | 6.0 | 4.9 |
| Midnight | 7.3 | 5.9 | |
| Monopoly | 5.7 | | |
| Mystic | | | |
| Nassau | 5.9 | | |
| Newport | | | |
| Nugget | | | |
| Parade | 5.6 | 6.5 | |
| Park | | 5.7 | |
| Ram I | 6.2 | 5.9 | |
| SO Common | 3.2 | | |
| Shasta | 5.7 | | |
| Sydsport | 6.0 | 6.3 | |
| Touchdown | 6.1 | 5.9 | |
| Trampas | | | 5.7 |
| Vantage | 3.6 | 5.8 | |
| Victa | 6.5 | 5.7 | |
| Wabash | 4.8 | | |

| Variety | Gervais Oregon 3 Year Mean | Marysville Ohio 5 Year Mean | Prince Frederick Maryland 4 Year Mean |
|---|---|---|---|
| Ba 72-500 | 2.8 | 2.8 | 2.3 |
| A-34 | | | |
| Adelphi | 2.4 | 2.7 | 1.9 |
| Admiral | | | |
| America | 2.5 | | |
| Aquila | | | |
| Banff | | | |
| Baron | | | |
| Birka | | | |
| Bonnieblue | | | |
| Bono | | | |
| Bristol | 2.8 | 2.7 | 2.1 |
| Columbia | | | |
| Eclipse | | | |
| Enmundi | | | |
| Fylking | | | |

TABLE 8-continued

Comparison of the Turf Quality of Ba 72-500 and Other Bluegrass Varieties in the U.S.A. and Canada

| | | | |
|---|---|---|---|
| Geary | | | |
| Geronimo | | | |
| Glade | 2.5 | | 1.8 |
| Gnome | 2.3 | | |
| Kenolue | 1.4 | | |
| Merion | | | |
| Merit | 2.4 | | 1.9 |
| Midnight | | | |
| Monopoly | | | |
| Mystic | | | |
| Nassau | | | |
| Newport | | 1.4 | |
| Nugget | | | |
| Parade | | 2.7 | |
| Park | | 2.1 | 1.7 |
| Ram I | | | |
| SO Common | | | |
| Shasta | | | |
| Sydsport | | | |
| Touchdown | | | |
| Trampas | | | |
| Vantage | | 2.6 | 1.8 |
| Victa | 2.2 | 2.6 | 2.1 |
| Wabash | | | |

Rating Scale: Larger number indicates higher quality.

Good turf performance under shady conditions is an important characteristic for broad, general usage of a bluegrass variety. Ba 72-500 performs very well under shady conditions as seen from the comparative test results in Tables 9 and 10.

TABLE 9

Turf Performance Ratings Under Natural Shade of Ba 72-5OO and Other Bluegrass Varieties at Marysville, Ohio.

| | Year 1 | Year 2 | Year 3 | Year 4 | 4 Yr Mean |
|---|---|---|---|---|---|
| Ba 72-500 | 2.1 | 2.3 | 2.5 | 2.5 | 2.4 |
| Merion | 1.8 | 1.6 | 2.0 | 1.8 | 1.8 |
| Fylking | 1.8 | 1.9 | 1.9 | 2.0 | 1.9 |
| A-34 | 2.0 | 2.2 | 2.6 | 2.7 | 2.4 |
| Park | 1.7 | 1.8 | 1.9 | 2.0 | 1.9 |
| Newport | 1.9 | 1.7 | 1.9 | 2.1 | 1.9 |
| Bristol | 1.8 | 2.1 | 2.2 | 1.8 | 2.0 |
| Enmundi | 2.0 | 2.0 | 2.2 | 2.5 | 2.2 |
| Bonnieblue | 2.0 | 1.7 | 2.0 | 1.7 | 1.9 |
| Touchdown | 1.8 | 2.1 | 2.1 | 1.7 | 1.9 |
| Aquila | 1.8 | 1.7 | 1.7 | 2.1 | 1.8 |
| Parade | 1.8 | 2.0 | 2.2 | 1.8 | 2.0 |
| Victa | 2.0 | 1.5 | 1.8 | 2.0 | 1.8 |
| LSD (.05) | | .46 | | .47 | |

Rated 1-4,4 = Best

TABLE 10

Turf Performance Ratings Under Natural Shade of Ba 72-500 and Other Bluegrass Varieties at Gervais, Oregon.

| | Quality | | | | | | |
|---|---|---|---|---|---|---|---|
| | Year 1 | | | | Year 2 | | |
| | June | Aug. | Oct. | Mean | Feb. | Sept | Mean |
| Ba 72-500 | 2.8 | 2.8 | 3.3 | 3.0 | 3.3 | 3.0 | 3.2 |
| Bristol | 2.5 | 2.8 | 2.3 | 2.6 | 3.0 | 1.7 | 2.4 |
| Gnome | 3.5 | 1.0 | 1.0 | 1.8 | 1.0 | 0.5 | .8 |
| Victa | 2.8 | 1.8 | 1.7 | 2.1 | 2.0 | 1.8 | 1.9 |
| LSD (.05) | .97 | .97 | .63 | | .95 | .96 | |

| | Quality | | |
|---|---|---|---|
| | Year 3 Feb. | Year 4 May | 4 Yr Mean |
| Ba 72-500 | 2.2 | 2.2 | 2.7 |
| Bristol | 2.0 | 2.3 | 2.3 |
| Gnome | 1.3 | 2.3 | 1.6 |
| Victa | 1.8 | 1.0 | 1.7 |

TABLE 10-continued

Turf Performance Ratings Under Natural Shade of Ba 72-500 and Other Bluegrass Varieties at Gervais, Oregon.

| | | |
|---|---|---|
| LSD (.05) | .83 | .80 |

Rated 1-4, 4 = Best

The new variety has a pleasant medium green color which can be maintained throughout the growing season and widely scattered locations in the U.S.A. and Canada as shown by the comparative test results in Table 11.

TABLE 11

Comparison of Turf Color of Ba 72-500 and Other Bluegrass Varieties at Various Locations in the U.S.A. and Canada.

| Variety | St. Louis Missouri 1 Year Mean | Truro Nova Scotia 1 Year Mean | Winnipeg Manitoba 1 Year Mean | Lincoln Nebraska 2 Year Mean |
|---|---|---|---|---|
| Ba 72-500 | 9.4 | 7.1 | 7.0 | 7.0 |
| A-34 | | | 6.3 | 6.5 |
| Adelphi | 9.4 | | | 7.2 |
| America | 9.4 | | | 7.0 |
| Aquila | | | 7.3 | 6.7 |
| Baron | 9.2 | | 7.3 | 6.9 |
| Birka | 9.1 | | | 6.7 |
| Bonnieblue | | | | 7.0 |
| Bono | 9.0 | | | |
| Bristol | 9.5 | | | 7.3 |
| Eclipse | | | | 7.0 |
| Enmundi | | | | 7.0 |
| Fylking | | | | 6.8 |
| Geronimo | | | | |
| Glade | 9.3 | | | 7.1 |
| Gnome | 9.3 | 7.5 | | |
| Kenblue | | | | |
| Merion | | | | 6.9 |
| Merit | 9.2 | | 7.2 | 7.0 |
| Midnight | | | 8.1 | 7.9 |
| Mystic | | | 6.5 | |
| Nassau | | | 7.2 | |
| Newport | | | | |
| Nugget | | | 7.3 | |
| Parade | | | | 6.8 |
| Park | 9.0 | | | 6.1 |
| Ram I | | | | 7.3 |
| Rugby | | | | 6.8 |
| Shasta | | | 7.2 | |
| Sydsport | 9.2 | | | 7.0 |
| Touchdown | 9.0 | | 6.6 | 6.8 |
| Trampas | | 6.9 | | |
| Vantage | 9.2 | | | 6.8 |
| Victa | 9.2 | 7.5 | | 6.9 |

| Variety | Agassiz British Columbia 1 Year Mean | Gervais Oregon 3 Year Mean | Marysville Ohio 2 Year Mean | Prince Frederick Maryland 3 Year Mean |
|---|---|---|---|---|
| Ba 72-500 | 5.5 | 7.2 | 8.1 | 7.7 |
| A-34 | | | | |
| Adelphi | | 7.6 | 8.4 | 7.4 |
| America | | 7.6 | 8.5 | |
| Aquila | | | | |
| Baron | | | 8.5 | |
| Birka | | | 8.1 | |
| Bonnieblue | | | | |
| Bono | 6.0 | | | |
| Bristol | 7.0 | 9.3 | 8.9 | 8.3 |
| Eclipse | | | 8.5 | |
| Enmundi | | | | |
| Fylking | | | | |
| Geronimo | 5.8 | | | |
| Glade | | 8.3 | 8.4 | 8.0 |
| Gnome | | 7.4 | 8.1 | |
| Kenblue | | 6.6 | 8.1 | |
| Merion | 5.7 | | | |
| Merit | 6.5 | 7.4 | | 7.4 |
| Midnight | | | 8.9 | |
| Mystic | | | | |

TABLE 11-continued

Comparison of Turf Color of Ba 72-500 and Other Bluegrass Varieties at Various Locations in the U.S.A. and Canada.

| | | | |
|---|---|---|---|
| Nassau | | | |
| Newport | 7.5 | | |
| Nugget | | | |
| Parade | | | |
| Park | | 8.1 | 6.8 |
| Ram I | | | |
| Rugby | | | |
| Shasta | | | |
| Sydsport | | 8.2 | |
| Touchdown | | 8.1 | |
| Trampas | | | |
| Vantage | | 8.5 | 6.8 |
| Victa | 7.1 | 8.4 | 7.6 |

Rating Scale: Larger number indicates darker green color.

Resistance to common turf diseases is important for consistent performance throughout the year and among locations. Comparisons of resistance to leaf spot (also known as melting out and crown rot) caused by the fungus *Helminthosporium vagans* are presented in Table 12.

TABLE 12

Comparison of Leafspot Disease Incidence on Ba 72-500 and Other Bluegrasses at Several Locations in the U.S.A. and Canada.

| Variety | St. Louis[a] Missouri 1 Year Mean | Beltsville[b] Maryland 1 Year Mean | Adelphia[b] New Jersey 1 Year Mean | Agassiz[c] British Columbia 1 Year Mean |
|---|---|---|---|---|
| Ba 72-500 | 3 | 7.7 | 7.0 | 3.0 |
| A-34 | | 5.3 | 4.3 | |
| Adelphi | 2 | 8.0 | 5.7 | |
| America | 8 | | | |
| Aquila | | | 6.3 | |
| Banff | | 5.3 | 7.0 | |
| Baron | 2 | 7.0 | 8.7 | |
| Birka | 5 | | 6.3 | |
| Bonnieblue | | | 7.0 | |
| Bono | 7 | | | 3.0 |
| Bristol | 2 | 7.0 | 8.3 | 2.3 |
| Columbia | | 5.7 | 6.3 | |
| Eclipse | | 7.7 | 9.0 | |
| Enmundi | | 7.0 | | |
| Fylking | | 6.7 | 6.3 | |
| Geary | | | 2.0 | |
| Geronimo | | | | 4.7 |
| Glade | 2 | 7.3 | 6.3 | |
| Gnome | 2 | 7.0 | 8.0 | |
| Kenblue | | 3.3 | 1.7 | |
| Merion | | 6.3 | 7.7 | 3.0 |
| Merit | 3 | 7.3 | 7.7 | 3.7 |
| Midnight | | 7.0 | 7.0 | |
| Monopoly | | 5.3 | 6.0 | |
| Nassau | | 7.7 | 7.4 | |
| Newport | | | | |
| Parade | | 6.0 | 5.0 | |
| Park | 52 | | | |
| Ram I | | 6.5 | 7.0 | |
| Rugby | | | 5.0 | |
| Shasta | | | 6.0 | |
| Sydsport | 3 | 7.3 | 6.3 | |
| Touchdown | 7 | 7.7 | | |
| Trenton | | | 6.0 | |
| Vantage | 7 | 5.0 | 2.0 | |
| Victa | 2 | 8.0 | 7.0 | |
| Wabash | | | 2.0 | |
| LSD (.05) | 7 | | 1.9 | |

| Variety | Gervais[a] Oregon 3 Year Mean | Marysville[a] Ohio 5 Year Mean | Accokeek[a] Maryland 2 Year Mean | Marysville[a] Ohio (Shade) 1 Year Mean |
|---|---|---|---|---|
| Ba 72-500 | 21 | 4 | 1 | 0 |
| A-34 | | | | |
| Adelphi | 46 | 9 | | |

TABLE 12-continued

Comparison of Leafspot Disease Incidence on Ba 72-500 and Other Bluegrasses at Several Locations in the U.S.A. and Canada.

| | | | | |
|---|---|---|---|---|
| America | 29 | | | 0 |
| Aquila | | | | |
| Banff | | | | |
| Baron | | | | |
| Birka | | | | 0 |
| Bonnieblue | | | | |
| Bono | | | | |
| Bristol | 8 | 5 | | 2 |
| Columbia | | | | |
| Eclipse | | | | |
| Enmundi | | | | |
| Fylking | | | | |
| Geary | | | | |
| Geronimo | | | | |
| Glade | 46 | | | 0 |
| Gnome | 76 | | | 0 |
| Kenblue | 75 | | | 67 |
| Merion | | | | |
| Merit | 65 | | | |
| Midnight | | | | |
| Monopoly | | | | |
| Nassau | | | | |
| Newport | 45 | | | |
| Parade | | 10 | | |
| Park | | 54 | | |
| Ram I | | | | |
| Rugby | | | | |
| Shasta | | | | |
| Sydsport | — | | | |
| Touchdown | | | | 0 |
| Trenton | | | | |
| Vantage | | 15 | 30 | |
| Victa | 70 | 7 | 12 | 0 |
| Wabash | | | | |
| LSD (.05) | 15 | 5 | 10 | 4 |

Ratings
[a]% of turf affected by disease
[b]1–9, 9 = least disease
[c]1–9, 9 = most disease Comparisons of resistance to powdery milkdew caused by *Erysiphe graminis*, rust caused by Puccinia spp., dollarspot caused by *Sclerotina homeocarpa*, stripe smut caused by *Ustilago striiformis*, and red thread caused by *Corticium fuciform* are presented in Tables 13–18.

TABLE 13

Comparison of Stem Rust (*Puccinia graminis*) Disease Incidence on Ba 72-500 and Other Bluegrasses at Adelphia, New Jersey

| | Test 1 | Test 2 |
|---|---|---|
| Ba 72-500 | 7.2 | 7.7 |
| Midnight | 7.O | 7.8 |
| Columbia | 6.7 | 7.8 |
| Banff | 6.5 | 7.7 |
| Bristol | 7.7 | 7.7 |
| Parade | 6.2 | 7.5 |
| Monopoly | 7.1 | 7.4 |
| Ram I | 7.0 | 7.3 |
| Victa | 5.6 | 7.2 |
| Merit | 5.7 | 7.0 |
| Baron | 6.4 | 7.0 |
| Nassau | 6.8 | 7.0 |
| Eclipse | 4.7 | 7.0 |
| Aquila | 6.9 | 7.0 |
| Bonnieblue | 5.4 | 7.0 |
| Adelphi | 7.1 | 6.9 |
| America | 7.4 | 6.9 |
| Vantage | 6.2 | 5.9 |
| Touchdown | 3.5 | 5.7 |
| Birka | 3.5 | 5.6 |
| Merion | 2.4 | 3.6 |
| LSD (.05) | 0.9 | 1.0 |

Rated 1–9,9 = No Disease

TABLE 14

Comparison of Rust (Puccinia spp.) Disease Incidence on Ba 72-500 and Other Bluegrasses.

| | Turf | Unmowed Spaced Plants | |
|---|---|---|---|
| Location | Aggasiz[a] British Columbia | Gervais[b] Oregon | Marysville[b] Ohio |
| | | Rating Years | |
| Variety | 2 Year Mean | 1 Year Mean | 1 Year Mean |
| Ba 72-500 | 1.3 | 1 | 17 |
| A-34 | | | 10 |
| Adelphi | | 23 | 10 |
| America | | 9 | |
| Bono | 2.1 | | |
| Bristol | 1.2 | 6 | 9 |
| Geronimo | 1.5 | | |
| Glade | | 4 | 13 |
| Gnome | | 13 | |
| Kenblue | | 30 | 24 |
| Merion | 2.8 | | 33 |
| Merit | 2.9 | 8 | |
| Newport | | 23 | |
| Nugget | | | 13 |
| Parade | | | 7 |
| Park | | | 32 |
| Vantage | | | 43 |
| Victa | | 9 | 18 |
| LSD (.05) | | 12 | 16 |

[a]Rated 1-9, 9 = most disease
[b]Rated as % of disease incidence

TABLE 15

Comparison of Dollarspot Disease Incidence on Ba 72-500 and Other Bluegrasses.

| Variety | Prince Frederick Maryland | Marysville Ohio |
|---|---|---|
| Ba 72-500 | 24 | 47 |
| Adelphi | 8 | 20 |
| America | | 13 |
| Baron | 50 | 23 |
| Birka | 6 | 47 |
| Bonnieblue | 10 | |
| Bono | 4 | 63 |
| Bristol | 6 | 17 |
| Columbia | 10 | |
| Eclipse | | 8 |
| Glade | | 40 |
| Gnome | | 22 |
| Kenblue | 8 | 37 |
| Merit | 4 | |
| Midnight | 6 | |
| Park | | 33 |
| Ram I | 40 | |
| Rugby | 12 | |
| Sydsport | | 43 |
| Touchdown | | 50 |
| Trenton | 28 | |
| Vantage | 11 | 15 |
| Victa | 5 | 23 |
| Wabash | 11 | |
| LSD (.05) | 19 | 24 |

Ratings: % of turf that is affected by disease.

TABLE 16

Comparison of Stripe Smut Disease Incidence on Ba 72-500 and Other Bluegrasses.

| Variety | Prince Frederick Maryland 3 Year Mean | Accokeek Maryland 2 Year Mean |
|---|---|---|
| Ba 72-500 | 0 | 2 |
| Bristol | 7 | |
| Mosa | 23 | |
| Vantage | | 3 |
| Victa | | 9 |

TABLE 16-continued

Comparison of Stripe Smut Disease Incidence on Ba 72-500 and Other Bluegrasses.

| Variety | Prince Frederick Maryland 3 Year Mean | Accokeek Maryland 2 Year Mean |
|---|---|---|
| LSD (.05) | 16 | 9 |

Rating: % of turf affected by disease.

TABLE 17

Comparison of Red Thread Disease Incidence on Ba 72-500 and Other Bluegrasses at Gervais, Oregon

| | Red Thread |
|---|---|
| Ba 72-500 | 0 |
| Victa | 10 |
| Bristol | 0 |
| Glade | 15 |
| Adelphi | 0 |
| Kenblue | 23 |
| Newport | 3 |
| America | 2 |
| Merit | 7 |
| Gnome | 0 |
| LSD (.05) | 13 |

Ratings % of turf affected by disease.

TABLE 18

Comparison of Powdery Mildew Disease Incidence on Ba 72-500 and Other Bluegrasses.

| | Greenhouse[a] | Natural Shade[b] | | |
|---|---|---|---|---|
| | Adelphia New Jersey | Gervais Oregon | Marysville Ohio | |
| Variety | 1 Year Mean | 1 Year Mean | 3 Year Mean | 2 Year Mean |
| Ba 72-500 | 5.4 | 3 | 3 | 0 |
| A-34 | 4.5 | | | |
| Adelphi | 0.8 | | | |
| America | 6.7 | | | 7 |
| Aquila | 8.7 | | | |
| Banff | 0.4 | | 15 | |
| Baron | 1.4 | | | |
| Birka | 5.7 | | | 2 |
| Bonnieblue | 0.8 | | | |
| Bristol | 6.4 | 3 | 10 | 1 |
| Columbia | 0.5 | | | |
| Eclipse | 6.9 | | | 3 |
| Enmundi | 6.9 | | | |
| Fylking | 1.3 | | | |
| Geronimo | | | | 40 |
| Glade | 7.0 | | 37 | 21 |
| Gnome | 1.7 | 78 | | 61 |
| Kenblue | | | | 2 |
| Kimono | 0.9 | | | |
| Majestic | 0.9 | | | |
| Merion | 0.9 | | | |
| Merit | 2.3 | | | |
| Midnight | 0.7 | | | |
| Monopoly | 5.9 | | 2 | |
| Mosa | | | | |
| Mystic | 8.3 | | | |
| Newport | | | 33 | |
| Nugget | 7.0 | | | |
| Parade | 2.2 | | | |
| Ram I | 7.2 | | | |
| Rugby | 0.6 | | 15 | |
| Shasta | 0.7 | | | |
| Sydsport | 6.1 | | | |
| Touchdown | | | | 0 |
| Vantage | 5.0 | | | |
| Victa | 1.9 | 35 | 47 | 52 |
| LSD (.05) | 0.8 | 21 | 16 | 6 |

| | Spaced Plants - Sun[b] | |
|---|---|---|
| | Prince Frederick Maryland | Marysville Ohio |
| | 1 Year | 2 Year |

TABLE 18-continued

Comparison of Powdery Mildew Disease Incidence on Ba 72-500 and Other Bluegrasses.

| Variety | Mean | Mean |
|---|---|---|
| Ba 72-500 | 0 | 0 |
| A-34 | 2 | 15 |
| Adelphi | 12 | 23 |
| America | | |
| Aquila | | |
| Banff | | |
| Baron | | |
| Birka | | |
| Bonnieblue | | |
| Bristol | 1 | 0 |
| Columbia | | |
| Eclipse | | |
| Enmundi | | |
| Fylking | | |
| Geronimo | | |
| Glade | 57 | 23 |
| Gnome | | |
| Kenblue | | 10 |
| Kimono | | |
| Majestic | | |
| Merion | | 5 |
| Merit | | |
| Midnight | | |
| Monopoly | | |
| Mosa | 58 | |
| Mystic | | |
| Newport | | |
| Nugget | | 3 |
| Parade | | 0 |
| Ram I | | |
| Rugby | | |
| Shasta | — | |
| Sydsport | | |
| Touchdown | | |
| Vantage | | 34 |
| Victa | | 13 |
| LSD (.05) | 25 | 12 |

[a]Rated 0–9, 9 = least disease
[b]Rated as % of turf affected by disease

Ba 72-500 has the ability to tolerate heat and drought stress as illustrated in Table 19.

TABLE 19

Comparison of Drought and Heat Tolerance of Ba 72-500 and Other Bluegrasses in Prince Frederick, Maryland.

| Variety | Test 1 4 Year Mean | Test 2 1 Year Mean | Test 3 3 Year Mean |
|---|---|---|---|
| Ba 72-500 | 20 | 0 | 27 |
| Adelphi | | | 36 |
| Bristol | 31 | | 36 |
| Glade | | | 49 |
| Merit | | | 43 |
| Mosa | 27 | | |
| Park | | | 39 |
| Vantage | | 50 | 39 |
| Victa | | 50 | 30 |
| LSD (.05) | 12 | 24 | 22 |

Rated as % brown turf due to drought and heat stress.

The low growth habit and slower vertical growth rate of Ba 72-500 indicates that it should withstand low mowing heights as well as possibly decrease the total number of mowings per year under favorable enviromental conditions, especially in comparison to the common type varieties of Kenblue, Newport, and Park as presented in Table 20.

TABLE 20

Comparison of Growth Habit of Ba 72-500 and Other Bluegrasses at Marysville, Ohio.

| Variety | Test 1 1 Year Mean[a] | Test 2 2 Year Mean[b] | Test 3 3 Year Mean[b] |
|---|---|---|---|
| Ba 72-500 | 2.0 | 1.4 | 66 |
| Adelphi | 2.0 | 2.4 | |
| America | 1.8 | | |
| Baron | 1.8 | | |
| Birka | 2.0 | | |
| Bono | 2.0 | | |
| Bristol | 2.0 | 2.0 | 74 |
| Eclipse | 2.0 | | |
| Fylking | | | 93 |
| Glade | 2.2 | | |
| Gnome | 2.0 | | |
| Kenblue | 2.9 | | |
| Merion | | | 96 |
| Merit | | | 78 |
| Newport | | | 84 |
| Parade | | | 100 |
| Park | | 2.2 | |
| Sydsport | 2.9 | 2.2 | |
| Touchdown | 1.9 | | 72 |
| Vantage | 2.0 | | |
| Victa | 2.7 | 2.0 | 84 |
| LSD (.05) | 1.9 | 2.0 | 77 |
| | 0.3 | 0.5 | 12 |

[a]Rated 1–5,5 = high growth, 1 = dwarf.
[b]Rated as height (mm) of turf about one week after last mowing.

The leaf texture of Ba 72-500 is similar to many bluegrass varieties when maintained under mowed turf conditions as the comparative test results show in Table 21.

TABLE 21

Comparison of Leaf Texture of Ba 72-500 and Other Bluegrasses Under Mowed Turf Conditions.

| Variety | St.Louis Missouri | Agassiz British Columbia | Marysville Ohio |
|---|---|---|---|
| Ba 72-500 | 4.3 | 6.0 | 5.0 |
| Adelphi | 5.3 | | |
| America | 6.0 | | |
| Baron | 4.6 | | |
| Birka | 6.0 | | |
| Bono | 5.6 | 6.7 | |
| Bristol | 5.3 | 7.0 | 5.0 |
| Fylking | | | 5.8 |
| Geronimo | | 5.7 | |
| Glade | 6.0 | | |
| Gnome | 4.3 | | |
| Kenblue | | | 5.5 |
| Merion | | 6.3 | 5.0 |
| Merit | 4.3 | 5.0 | 5.0 |
| Newport | | | 5.0 |
| Park | 6.0 | | |
| Sydsport | 5.0 | | 5.0 |
| Touchdown | 5.0 | | |
| Vantage | 6.0 | | 5.3 |
| Victa | 4.4 | | 4.8 |
| LSD (.05) | 0.7 | | 0.4 |

Ratings: 1–9,9 = finest texture.

Ba 72-500 has a good level of seed yielding ability which should make it an economically feasible variety to produce for commercial markets as shown in Table 22.

TABLE 22

Seed Yield Comparisons of Ba 72-500 and Other Bluegrass Varieties in Oregon

| Location | Gervais | | | La Grande | | | |
|---|---|---|---|---|---|---|---|
| Seeded Harvest Year | Year 1 | Year 2 | Mean | Year 1 | Year 2 | Mean | Madras Year 1 |
| Variety | | | | | | | |
| Ba 72-500 | 559 | 757 | 658 | 876 | 857 | 867 | 1113 |
| Victa | 780 | 1394 | 1087 | 1419 | 1200 | 1310 | 1324 |

TABLE 22-continued

Seed Yield Comparisons of Ba 72-500 and Other Bluegrass Varieties in Oregon

| Location | Gervais | | | La Grande | | | Madras |
|---|---|---|---|---|---|---|---|
| Seeded | Year | Year | | Year | Year | | |
| Harvest Year | 1 | 2 | Mean | 1 | 2 | Mean | Year 1 |
| Newport | 435 | 1256 | 846 | | | | |
| Bristol | 347 | 808 | 578 | 1089 | 970 | 1030 | |
| Mosa | 322 | 1060 | 691 | | | | |
| Julia | 296 | 1016 | 656 | | | | |
| Baron | | | | | | | 1194 |
| Trampas | | | | | | | 388 |
| LSD (.05) | 140 | 134 | | 149 | 181 | 220 | |

Ratings: Pounds per acre of conditioned seed.

The low susceptibility of Ba 72-500 to rust and lodging under typical seed field conditions should aid in producing enconomical seed crops as indicated by the comparative results in Table 23.

TABLE 23

Plant Characteristics of Ba 72-500 and Other Bluegrass Varieties at Gervais, Oregon Under Seed Production Conditions.

| | Rust | Lodging | |
|---|---|---|---|
| | | Year 1 | Year 2 |
| Ba 72-500 | 1 | 2.5 | 0.2 |
| Victa | 2 | 2.0 | 0 |
| Bristol | 4 | 4.0 | 1 |
| Newport | 4 | 4.0 | 1 |
| Mosa | 4 | 2.0 | 0 |
| Julia | 4 | 5.0 | 4 |

Ratings
Rust: 1–4.4 = very susceptible
Lodging: 0–5.5 = severe lodging

What is claimed is:

1. A variety of bluegrass plant, substantially as shown and described, characterized particularly by a high level of resistance to disease and especially leaf spot disease, a desirable green color throughout the growing season, a high quality persistent turf under a wide variety of environmental conditions including shady conditions and a good-to-medium level of seed yielding capacity.

* * * * *

FIG. 1
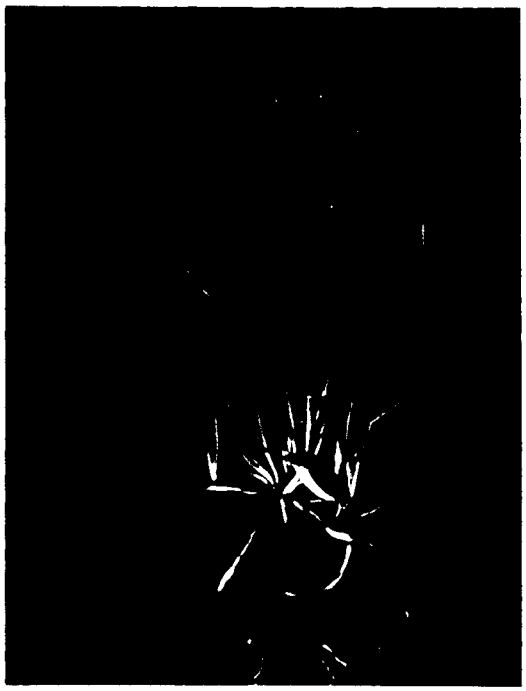
FIG. 2
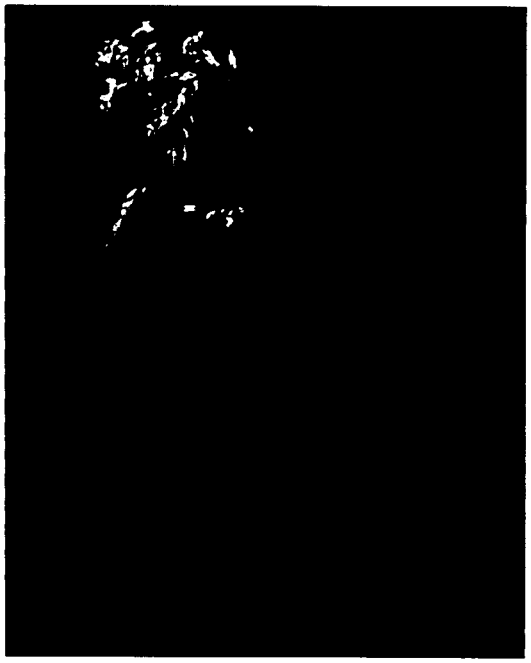
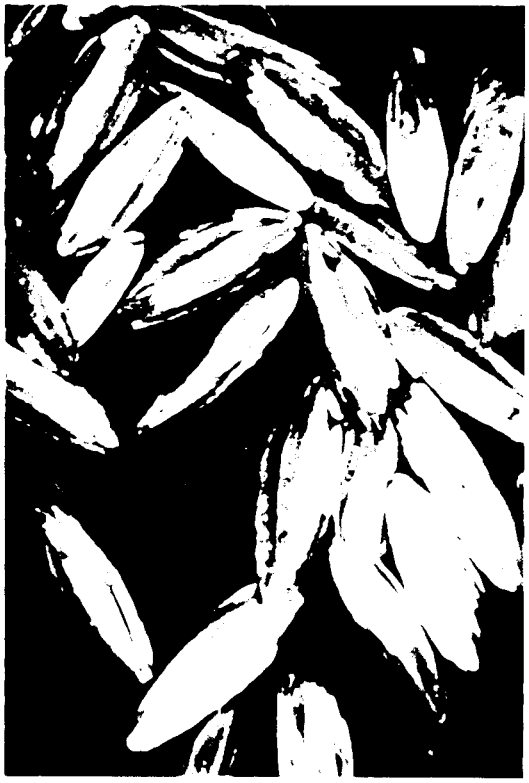
FIG. 3
ok to print
7/26/88
Rem